United States Patent [19]

Matta et al.

[11] 4,454,751

[45] Jun. 19, 1984

[54] EXTRUDATE SWELL RHEOMETER AND METHOD OF USING SAME

[75] Inventors: Joseph E. Matta, Bel Air; Jeffrey L. Harris, Edgewood, both of Md.

[73] Assignee: The United States of America as represented by the Secretary of the Army, Washington, D.C.

[21] Appl. No.: 431,870

[22] Filed: Sep. 30, 1982

[51] Int. Cl.³ .................. G01N 11/04; G01N 11/02; G01D 9/42

[52] U.S. Cl. .................. 73/56; 73/54; 346/107 R

[58] Field of Search .................. 73/56, 54, 55; 346/107 R, 107 MP

[56] References Cited

U.S. PATENT DOCUMENTS 3,832,886  9/1974  Pliskin .................. 73/56

4,157,029  6/1979  Leca et al. .................. 73/55
4,403,502  9/1983  Lindt .................. 73/55

*Primary Examiner*—Gerald Goldberg
*Assistant Examiner*—Anna M. Schrichte
*Attorney, Agent, or Firm*—Robert P. Gibson; Anthony T. Lane; Harold H. Card, Jr.

[57] ABSTRACT

A rheometer for measuring the extrudate swell of polymeric solutions. The rheometer has an upper and lower transparent reservoir with a capillary tube therebetween. The flow of solution between reservoirs from upper to lower is provided by gas pressure. Initially, the swell is photographed and the lower reservoir is then filled with an immiscible Newtonian fluid. In sequence the flow is again started and a second photograph is taken. The first and second swell are measured, and the results applied to a formula to determine the first normal stress difference of the polymeric solution.

12 Claims, 3 Drawing Figures

EXTRUDATE SWELL RHEOMETER AND METHOD OF USING SAME

GOVERNMENTAL INTEREST

The invention described herein may be manufactured, used and licensed by or for the Government for governmental purposes without the payment to us of any royalties thereon.

FIELD OF THE INVENTION

This invention relates to a rheological measuring apparatus, and more particularly to an apparatus for accurately measuring the first normal stress difference of a polymeric solution, and method of using same.

BACKGROUND OF THE INVENTION

Most polymeric solutions demonstrate non-Newtonian flow and a measurement of viscosity and first normal stress difference typically requires expensive and cumbersome equipment. Commercially available equipment includes cone and plate-type shear rheometers to measure both the viscosity and first normal stress difference of a polymeric solution. In a cone and plate-type shear rheometer, a small quantity of fluid is sheared between a cone and rotating plate and the normal and tangential forces exerted on the plate are measured and used to deduce the first normal stress difference and viscosity, respectively. However, the cone and plate-type shear rheometers suffer from several drawbacks. The cone and plate rheometers are expensive and of considerable size, thus detracting from their usefulness and availability.

In addition, due to the size of cone and plate rheometers, the measurement of the first normal stress difference and viscosity with respect to toxic fluids exhibiting non-Newtonian flow is not desirable and in some instances dangerous since such rheometers cannot fit into a conventional size glovebox. Since the fluid often spins out from the plate as it is rotated at high revolutions, its use and application to the measurement of viscosity and first normal stress difference with toxic fluids is limited, and in some cases is to be avoided.

A variety of other instruments are available for the measurement of viscosity of polymeric fluids, however, no method has yet been developed to permit these instruments to measure the first normal stress difference and there is no corollary yet available to equate the data derived from these instruments with existing data to determine the first normal stress difference.

OBJECT OF THE INVENTION

An object of the present invention is to provide a novel apparatus and method for the measurement of the first normal stress difference of a polymeric solution by measurement of the extrudate swell.

A further object of the present invention is to provide a novel apparatus and method for the measurement of the first normal stress difference of toxic fluids by measurement of the extrudate swell.

A still further object of the present invention is to provide a novel apparatus and method for accurately measuring smaller values of the first normal stress difference of polymeric solutions than possible with conventional available rheometers.

SUMMARY OF THE INVENTION

These and other objects of the present invention are achieved by an apparatus comprised of a first reservoir vertically-disposed above a second transparent reservoir and connected to one another by a capillary tube. The polymeric solution to be tested is introduced into the first reservoir, pressurized by means of a three-way valve to provide constant air pressure to the first reservoir and permit of the instantaneous termination of flow through the capillary tube by means of an atmosphere vent.

The method of the present invention includes first ejecting the polymeric solution to be tested vertically downward from the first reservoir into a fluidless second reservoir with the second reservoir being vented to the atmosphere. The swell of the extruded fluid jet emerging from the capillary is photographed and the weight of the polymeric solution gathered in the second reservoir is weighed to determine the flow rate. Thereafter, polymeric solution is ejected vertically downward through the capillary tubing into an immiscible fluid of less density than the polymeric solution contained in the first reservoir. Again, the swell of the extruded fluid at the capillary opening in the second reservoir is photographed and the weight of the polymeric solution accumulating in the second reservoir weighed to determine the flow rate. The maximum swell is measured from the photographs and this data is used to calculate the first normal stress difference, as more fully hereinafter discussed.

DETAILED DESCRIPTION OF THE DRAWINGS

FIG. 1 is a vertical cross-sectional view of the apparatus.

FIG. 2 is a plot of the die-swell ratios versus the elastic shear compliance; and FIG. 3 is a plot of the first normal stress difference versus the shear rate.

Figure 1:
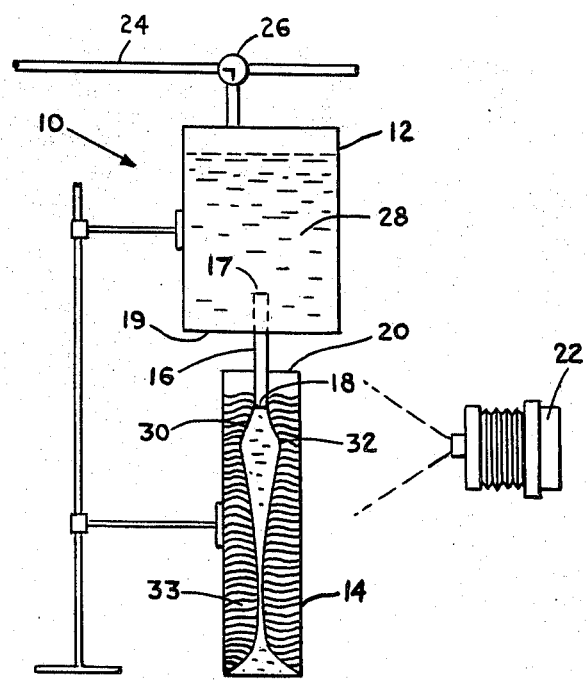
FIG. 1 discloses an extrudate swell rheometer 10 comprising a first reservoir 12 vertically-disposed above a second reservoir 14. Reservoirs 12 and 14 are in intimate fluid communication by means of a vertically-disposed capillary tube 16 having an upper opening 17 and a lower opening 18 and secured to reservoir 12 such that the upper opening 17 of capillary tube 16 extends into reservoir 12. The capillary tube 16 extends vertically downwardly from a lower end portion 19 of reservoir 12 such that lower opening 18 of the capillary tube 16 extends below an upper lip 20 of reservoir 14.

The fluid reservoir 12 is a sealed reservoir having secured thereto, a pressure regulated air line thus permitting the pressurization of fluid reservoir 12. The fluid reservoir 14 is transparent and has a height substantially greater than its diameter.

In utilizing the disclosed apparatus, a camera 22 is required to be securely mounted proximate to fluid reservoir 14 at a height proximate to the lower opening 18 of capillary 16.

A pressurized gas line 24 including a three-way valve 26 is provided to permit fluid reservoir 12 to be pressurized, and thus cause the flow of a polymeric solution 28 contained therein through the capillary 16 and into the fluid reservoir 14. The three-way valve 26 also permits venting of the fluid reservoir 12 to the atmosphere and thereby to quickly terminate the flow of polymeric solution 28 through capillary 16 into fluid reservoir 14.

In operation, the fluid reservoir 12 is filled with a polymeric solution to tested. The camera 22 is positioned near the lower fluid reservoir 14, proximate to the lower opening 18 of the capillary tube 16. In the first step, the fluid reservoir 14 is devoid of any liquid fluid and contains only air. The three-way valve 26 is adjusted to pressurized fluid reservoir 12 thereby causing the polymeric solution 28 to be ejected downwardly through the capillary 16 and extruded out of lower opening 18 of the capillary tube 16. As the extruded fluid jet of polymeric solution 28 is ejected out of capillary 16, the fluid jet swells to a diameter greater than the inner diameter of capillary 16. Such swell 30, as depicted in FIG. 1, is photographed by camera 22. The photograph from camera 22 permits measurement of the largest extruded jet diameter 32 of the swell 30. Such jet diameter 32 to the known inner diameter of capillary 16 results in a die swell ratio of the polymer solution 28.

In a second step of the method of the present invention, an immiscible fluid 33 is introduced into the fluid reservoir 14. The immiscible fluid 33 should have a density less than the density of polymeric solution 28. Further, the depth of the immiscible fluid 33 in fluid reservoir 14 must be such that the lower opening 18 of the capillary tube 16 is below the surface level of the immiscible fluid 33. In this context, the polymeric solution 28 is ejected downwardly through the capillary tube 16 and the extruded jet diameter 32 of swell 30 in the immiscible fluid 33 is measured from the photograph taken by camera 22.

It can be seen that the height of reservoir 14 may vary, but that it must be sufficient to permit the polymeric solution to reach steady state flow such that the swell 30 is formed and is not influenced by the reservoir.

The amount of polymeric solution collected in fluid reservoir 14 during the course of both steps is weighed in order to determine the flow rate of polymeric solution 28 from the fluid reservoir 12 into the fluid reservoir 14. From the data of the steps of the present invention, the following empirical relationship was developed which permits the determination of the elastic shear compliance from which the normal stress difference can be deduced, given by Equation (1).

$$(D_L/D_a)^6 - 1 = 30(\Delta p/p_s)^{-1}([p_s g^2 N_n^2] J_e)^{3/5} \qquad (1)$$

where D is the die swell ratio of the polymeric solution 28 in immiscible fluid 33;

$D_a$ is the die swell ratio of polymeric solution 28 in air;

$\Delta p$ is the density difference between the extruded fluid density $p_s$ and the immiscible Newtonian fluid density p;

$N_n$ is the viscosity of the immiscible Newtonian fluid; and g is the gravitational constant necessary to dimensionalize the expression.

The aforementioned equation (1) permits the calculation of the elastic shear compliance $J_e$. Therefore, using equation (1), it is possible to measure the first normal stress difference using the extruded swell setup since $\Delta p$ is easily determined and one can calculate the elastic shear stress compliance $J_e$ from equation (1) after measuring the die swell ratios of the polymeric solution 28 in air and in the immiscible Newtonian fluid. Once the constant elastic shear compliance $J_e$ is determined, one can obtain the first normal stress difference $N_1$ from the following equation (2):

$$N_1 = 2J_e \sigma^2 \qquad (2)$$

after the shear stress $\sigma$ is measured using standard capillary flow or other techniques.

Figure 2:
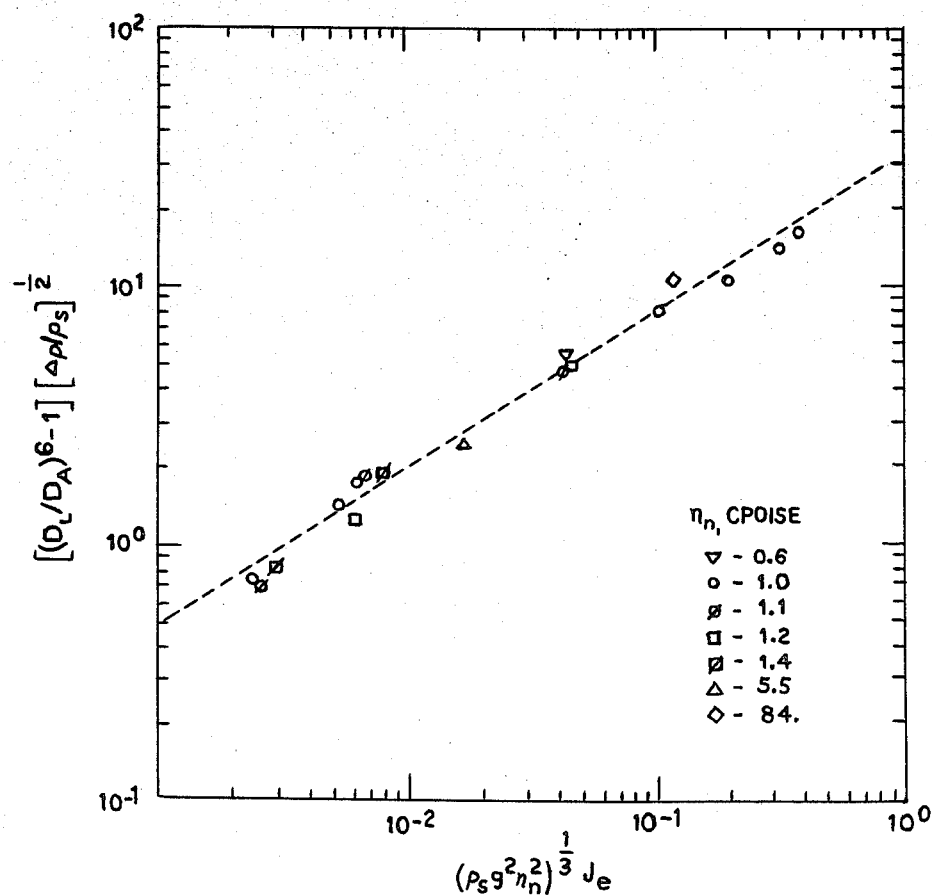
Figure 3:
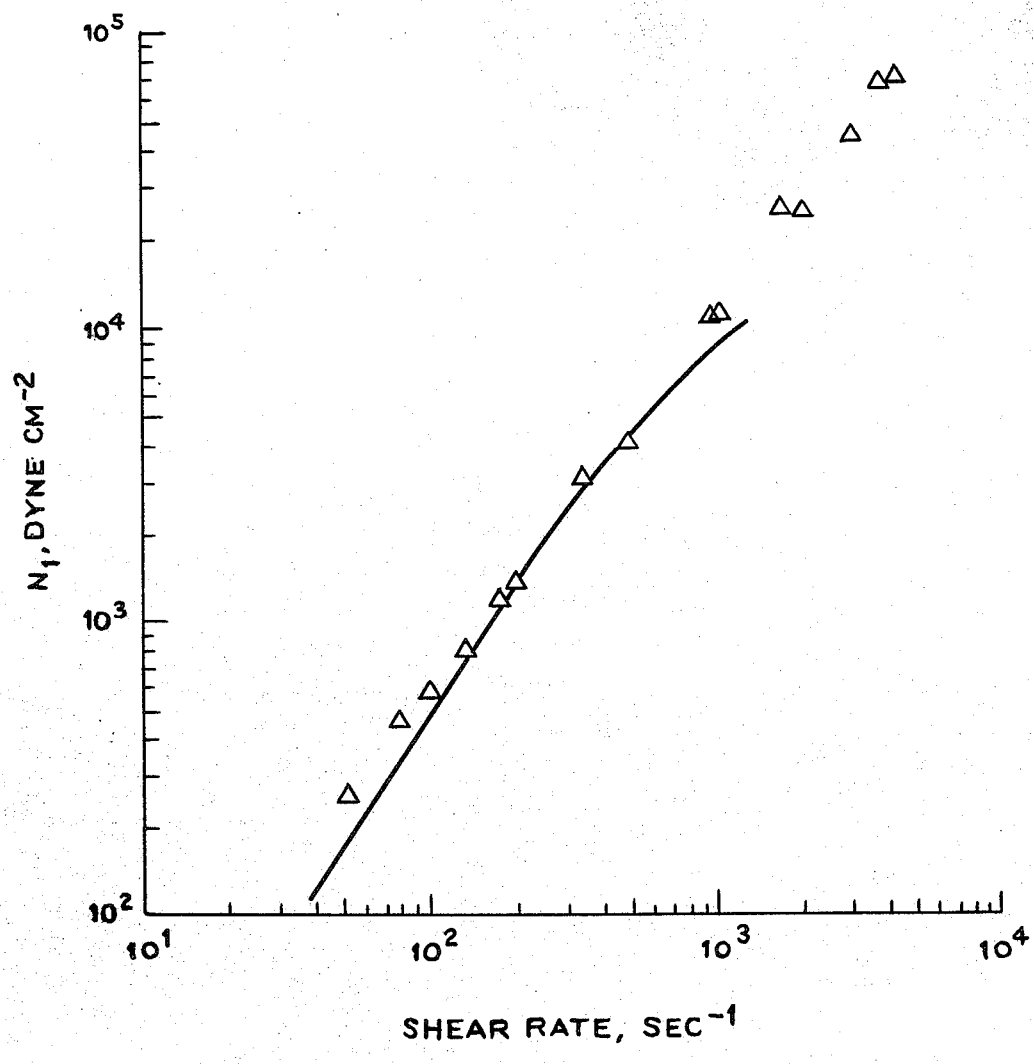

The empirical relationship from equation (1) for the various polymeric solutions tested is shown in FIG. 2. FIG. 3 shows a comparison of the first normal stress difference $N_1$, using the extrudate swell rheometer data ($\Delta$) and data from conventional cone and plate rheometer measurements (solid line). The agreement in the data is indicative of the usefulness of the extrudate swell rheometer to measure the first normal stress difference of a polymeric solution when sheared.

Furthermore eq(1) shows that one can magnify the swell effect by increasing the viscosity $N_n$ of the immiscible fluid 33 and thus by using immiscible fluids 33 with large values of viscosity it is possible to measure very small values of first normal stress difference $N_1$.

What is claimed:

1. A rheometer for measuring the extrudate swell of polymeric solutions, comprising:
    a first fluid reservoir for said test polymeric solution;
    a second fluid reservoir disposed beneath said first reservoir;
    conduit means for fluid communication between said first and second fluid reservoirs;
    means for initiating flow of said polymeric solution from said first fluid reservoir to said second fluid reservoir; and
    means for imaging said extrudate swell of said polymeric solution exiting said conduit means into said second fluid reservoir.

2. The apparatus in accordance with claim 1 wherein said conduit means between said first and second fluid reservoir is a capillary tube said capillary tube extending into said second fluid reservoir.

3. The apparatus in accordance with claim 1 wherein said first fluid reservoir is capable of being pressurized.

4. The apparatus in accordance with claim 1 or 3 wherein said means for initiating flow of said polymeric solution from said first fluid reservoir to said second fluid reservoir comprises a pressure regulated gas line having a valve means for pressurizing and venting said first fluid reservoir, said pressure regulated gas line being removably secured to said first fluid reservoir.

5. The apparatus in accordance with claim 1 wherein said second fluid reservoir is transparent.

6. The apparatus in accordance with claim 1 wherein said means for imaging said extrudate swell of said polymeric solution exiting said conduit means includes a camera.

7. A method for measuring the first normal stress difference of a polymeric solution comprising:
    placing said polymeric solution in a first reservoir in fluid communication by a conduit means with a second reservoir;
    pressuring said first reservoir to initiate a first flow of said polymeric solution through said conduit means into an empty second reservoir thereby forming a first extrudate swell upon exiting said conduit means;
    imaging said first extrudate swell of said polymeric solution;

introducing into said second reservoir, an immiscible Newtonian fluid having a density less than said polymeric solution;

pressuring said first reservoir to initiate a second flow of said polymeric solution through said conduit means into said second reservoir thereby forming a second extrudate swell upon exiting said conduit means;

imaging said second extrudate swell of said polymeric solution;

measuring said first and second extrudate swell to obtain maximum diameter of said extrudate swell;

determining elastic shear compliance in accordance with the following equation: (1)
$(D_L/D_a)^6 - 1 = 30(\Delta p/p_s)^{-1}([p_s g^2 N_n^2]^{\frac{1}{4}} J_e)^{3/5}$;
wherein $D_L$ is the die swell ratio of the polymeric solution in the immiscible fluid;

$D_a$ is the die swell ratio of the polymeric solution in gas;

$\Delta p$ is the density difference between the polymeric solution $p_s$ and the immiscible Newtonian fluid;

$N_n$ is the viscosity of the immiscible Newtonian fluid and g is the gravitational constant and $J_e$ is the elastic shear compliance; and determining first normal shear difference in accordance with the equation;
$N_1 = 2 J_e \sigma^2$, wherein
$N_1$ is the first normal stress difference and
$\sigma$ is the shear stress measured for polymeric solutions using standard capillary flow techniques.

8. A method for measuring the first normal stress difference of a polymeric solution in accordance with claim 7 wherein said pressure to initiate said first flow of polymeric solution and to initiate said second flow of polymeric solution are equal.

9. A method for measuring the first normal stress difference of a polymeric solution in accordance with claim 7 wherein the temperature of said polymeric solution in said first flow and said second flow are equal.

10. Method for measuring the first normal stress difference of a polymeric solution in accordance with claim 7 wherein the temperature of said polymeric solution and temperature of said immiscible Newtonian fluid are equal.

11. The method of claim 7 wherein said conduit means is extended below the level of an immiscible Newtonian fluid during said second flow of said polymeric solution.

12. The apparatus of claim 2 wherein said capillary tube extends into said second reservoir below the level of an immiscible Newtonian fluid.

* * * * *